(12) United States Patent
Shirakami et al.

(10) Patent No.: US 11,684,683 B2
(45) Date of Patent: Jun. 27, 2023

(54) ASTATINE SOLUTION AND METHOD FOR PRODUCING SAME

(71) Applicant: OSAKA UNIVERSITY, Suita (JP)

(72) Inventors: Yoshifumi Shirakami, Suita (JP); Tadashi Watabe, Suita (JP); Kazuko Kaneda, Suita (JP); Eku Shimosegawa, Suita (JP); Atsushi Shinohara, Suita (JP); Jun Hatazawa, Suita (JP)

(73) Assignee: OSAKA UNIVERSITY, Suita (JP)

( * ) Notice: Subject to any disclaimer, the term of this patent is extended or adjusted under 35 U.S.C. 154(b) by 310 days.

(21) Appl. No.: 16/958,147

(22) PCT Filed: Dec. 28, 2018

(86) PCT No.: PCT/JP2018/048442
§ 371 (c)(1),
(2) Date: Jun. 25, 2020

(87) PCT Pub. No.: WO2019/131998
PCT Pub. Date: Jul. 4, 2019

(65) Prior Publication Data
US 2020/0360546 A1    Nov. 19, 2020

(30) Foreign Application Priority Data

Dec. 29, 2017   (JP) .............................. JP2017-255109

(51) Int. Cl.
*A61K 51/12* (2006.01)
*A61K 47/22* (2006.01)
(52) U.S. Cl.
CPC ............ *A61K 51/121* (2013.01); *A61K 47/22* (2013.01)

(58) Field of Classification Search
CPC .............................. A61K 51/121; A61K 47/22
USPC ........................................................ 424/1.11
See application file for complete search history.

(56) References Cited

U.S. PATENT DOCUMENTS 5,314,678 A * 5/1994 Grummon .......... A61K 51/1262
424/1.61
2009/0304585 A1   12/2009 Zalutsky et al.

FOREIGN PATENT DOCUMENTS

| EP | 3663307 A1 | 6/2020 | |
|---|---|---|---|
| JP | 2009-521469 A | 6/2009 | |
| JP | 2017-507929 A | 3/2017 | |
| JP | 2017-528512 A | 9/2017 | |
| WO | WO-2011147762 A2 * | 12/2011 | ............. A61K 51/08 |
| WO | WO 2015/120458 A1 | 8/2015 | |
| WO | WO 2015/195042 A1 | 12/2015 | |
| WO | WO 2017/089492 A1 | 6/2017 | |
| WO | WO 2019/027059 A1 | 2/2019 | |

OTHER PUBLICATIONS

Petrich et al. Eur. J. Nucl. Med. (2002) 29, 842-854. (Year: 2002).*
(Continued)

*Primary Examiner* — Michael G. Hartley
*Assistant Examiner* — Sean R Donohue
(74) *Attorney, Agent, or Firm* — Leydig, Voit & Mayer, Ltd.

(57) ABSTRACT

The invention provides a method for producing a solution containing $^{211}At^-$ (astatide ion) at a high radiochemical purity by using $^{211}At$ obtained by a nuclear reaction as a starting material, including a step of adding a reducing agent to a solution containing an impurity derived from $^{211}At$. The invention also provides a solution containing $^{211}At^-$ (astatide ion) at a radiochemical purity of not less than 30%.

12 Claims, 7 Drawing Sheets

(56) References Cited

OTHER PUBLICATIONS

Downs et al., "The Chemistry of Chlorine, Bromine, Iodine and Astatine," (Pergamon International Library of Science, Technology, Engineering and Social Studies, 1973), pp. 1573-1594.
Shirakami, "Radiolabeling of small molecules with astatine ($^{211}$At) for theranostics," (Mar. 19, 2018) [obtained at: https://researchmap.jp/e5221/presentations/22036925/attachment_file.pdf].
Visser et al., "The Nature of the Astatine-Protein Bond," *International Journal of Applied Radiation and Isotopes*, 32(12): 905-912 (1981).
European Patent Office, Extended European Search Report in European Patent Application No. 18894698.2 (dated Jul. 14, 2021).
Aaij et al., "The Preparation of Astatine Labelled Proteins," *International Journal of Applied Radiation and Isotopes*, 26(1): 25-30 (1975).
Carlin et al., "In Vitro Cytotoxicity of $^{211}$At-Astatide and $^{131}$I-Iodide to Glioma Tumor Cells Expressing the Sodium/Iodide Symporter," *J. Nucl. Med.*, 44(11): 1827-1838 (2003).
Shiozaki et al., "Functional analysis and clinical significance of sodium iodide symporter expression in gastric cancer," *Gastric Cancer*, 22(3): 473-485 (2019).
Spetz et al., "Biodistribution and Dosimetry of Free $^{211}$At, $^{125}$I$^-$ and $^{131}$I$^-$ in Rats," *Cancer Biother. Radipharm.*, 28(9): 657-664 (2013).
Japanese Patent Office, International Search Report in International Patent Application No. PCT/JP2018/048442 (dated Mar. 12, 2019).
Japanese Patent Office, International Preliminary Report on Patentability in International Patent Application No. PCT/JP2018/048442 (dated Aug. 2, 2019).

\* cited by examiner (a) ascorbic acid group (b) control group a) changes in tumor size b) changes in body weight

US 11,684,683 B2

ASTATINE SOLUTION AND METHOD FOR PRODUCING SAME

CROSS-REFERENCE TO RELATED APPLICATIONS

This patent application is the U.S. national phase of International Patent Application No. PCT/JP2018/048442, filed on Dec. 28, 2018, which claims the benefit of Japanese Patent Application No. 2017-255109 filed on Dec. 29, 2017, which are incorporated by reference in their entireties herein.

TECHNICAL FIELD

The present invention relates to a solution containing $^{211}At^-$ (astatide ion) at a high radiochemical purity, and a production method thereof.

BACKGROUND ART

Radioisotope (RI) internal radiotherapy using sodium iodide ($Na^{131}I$) is widely used for treating thyroid gland diseases such as thyroid cancer and hyperthyroidism (Graves' disease, etc.). The thyroid gland takes in iodide ions through a sodium iodide symporter (hereinafter abbreviated as NIS). Thus, when $Na^{131}I$ is administered, iodide ion ($^{131}I^-$) accumulates specifically in the thyroid gland and thyroid cancer, and can treat by irradiating the affected area with β rays emitted from inside the body. However, internal radiotherapy using $Na^{131}I$ requires hospitalization of patients, the patients are isolated in a special room for radiation control, and multiple administrations associated with recurrence and discontinuation of treatment due to the emergence of drug resistance pose problem. One of the factors of these problems is considered to be the insufficient cell killing ability of β-ray released by $^{131}I$.

On the other hand, astatine-211 ($^{211}At$) is an RI that releases α-ray with higher cell killing ability than β-ray, and the development of RI internal radiotherapy using $^{211}At$-labeled compound or astatide ion ($^{211}At^-$) is expected.

Patent document 1 discloses a composition containing a halogen compound and recites astatine as one of the halogen compounds. However, it does not specifically disclose an astatine solution or a production method thereof.

Non-patent document 1 discloses experimental measurement results of distribution and radiation dose in the body of rats after $^{211}At$ administration. It describes that $^{211}At$ was produced by $^{209}Bi(\alpha,2n)^{211}At$ reaction, but does not describe addition of a reducing agent in the production step.

Non-patent document 2 discloses experimental measurement results of in vitro cytotoxicity of astatide against glioma cells expressing the sodium iodide symporter. It is described that $^{211}At$ was produced by $^{209}Bi(\alpha,2n)^{211}At$ reaction, and after isolation, $Na_2SO_3$ was added. However, in this document, effects on radiochemical purity by the addition of reducing agents have not been investigated.

Non-patent document 3 describes that expression of NIS is observed in stomach cancer, breast cancer, lung cancer, prostate cancer, colon cancer, ovarian cancer and the like.

DOCUMENT LIST

Patent Document patent document 1: National Publication of International Patent Application No. 2017-507929

Non-Patent Documents non-patent document 1: Spetz J, et al., Cancer Biotherapy and Radiopharmaceuticals, Volume 28, Number 9, 2013, 657-664 non-patent document 2: Carlin S, et al., The Journal of Nuclear Medicine, Vol. 44, No. 11, November 2003, 1827-1838 non-patent document 3: Atsushi Shiozaki, et al., Functional analysis and clinical significance of sodium iodide symporter expression in gastric cancer, Gastric cancer, https://doi.org/10.1007/s10120-018-0874-2, published online: 6 Sep. 2018

SUMMARY OF INVENTION

Technical Problem

The present invention aims to provide an astatine solution that can be used in RI internal radiotherapy and the like for the treatment of thyroid gland disease and the like, and a production method thereof.

Solution to Problem $^{211}At$ can generally be produced by a nuclear reaction. For example, a production method in which helium is accelerated by an accelerator such as a cyclotron, irradiated to a target substance bismuth-209 ($^{209}Bi$), and $^{211}At$ is produced in the target substance by the nuclear reaction of $^{209}Bi(\alpha, 2n)^{211}At$, the target substance is evaporated by heating to separate $^{211}At$, and $^{211}At$ is dissolved in a solvent such as water to give a $^{211}At$ solution is known.

However, the present inventors have conducted intensive studies and newly found that the $^{211}At$ solution produced by the conventional method as described above has a low radiochemical purity (see Experimental Example 1 described later), and a $^{211}At$ solution having such low radiochemical purity shows weak accumulation of radioactivity in the thyroid gland in an in vivo experiment using rats (see Experimental Example 7 described later).

The present inventors have conducted further studies based on the findings, and found that a $^{211}At$ solution with a high radiochemical purity can be produced by adding a reducing agent to a $^{211}At$ solution, and further, that the $^{211}At$ solution with a high radiochemical purity, which is produced by the method, shows enhanced accumulation of radioactivity in the thyroid gland after administration, as compared with one produced by the conventional method, and completed the present invention.

That is, the present invention provides the following.

[1] A method for producing a solution comprising $^{211}At^-$ (astatide ion) at a high radiochemical purity by using $^{211}At$ obtained by a nuclear reaction as a starting material, the method comprising a step of adding a reducing agent to a solution comprising an impurity derived from $^{211}At$.

[2] The method of the above-mentioned [1], wherein the reducing agent is a physiologically acceptable reducing agent.

[2-1] The method of the above-mentioned [2], wherein the reducing agent is an organic reducing agent or an inorganic reducing agent.

[2-2] The method of the above-mentioned [2-1], wherein the inorganic reducing agent is iron(II) sulfate.

[3] The method of the above-mentioned [1], wherein the reducing agent is a physiologically acceptable organic reducing agent.

[4] The method of the above-mentioned [1], wherein the reducing agent is selected from the group consisting of ascorbic acid, a salt with ascorbic acid, cysteine, glutathione and iron(II) sulfate.

[5] The method of the above-mentioned [1], wherein the reducing agent is ascorbic acid or sodium ascorbate.

[6] The method of any of the above-mentioned [1] to [5], further comprising a step of adjusting to neutral or weakly alkaline by adding a pH adjuster or buffer.

[7] A solution comprising $^{211}At^-$ (astatide ion) at a radiochemical purity of not less than 30%.

[8] A solution comprising $^{211}At^-$ (astatide ion) at a high radiochemical purity, which solution is produced by the method of any of the above-mentioned [1] to [6].

Advantageous Effects of Invention

According to the production method of the present invention, a solution containing $^{211}At^-$ (astatide ion) at a high radiochemical purity can be produced.

A solution containing $^{211}At^-$ (astatide ion) at a high radiochemical purity produced by the production method of the present invention is useful in RI internal radiotherapy and the like for the treatment of thyroid gland diseases.

A solution containing $^{211}At^-$ (astatide ion) at a high radiochemical purity which is produced by the production method of the present invention is useful in RI internal radiotherapy and the like for the treatment of stomach cancer, breast cancer, lung cancer, prostate cancer, colon cancer, ovarian cancer and the like that show expression of NIS.

DESCRIPTION OF EMBODIMENTS

Figure 1:
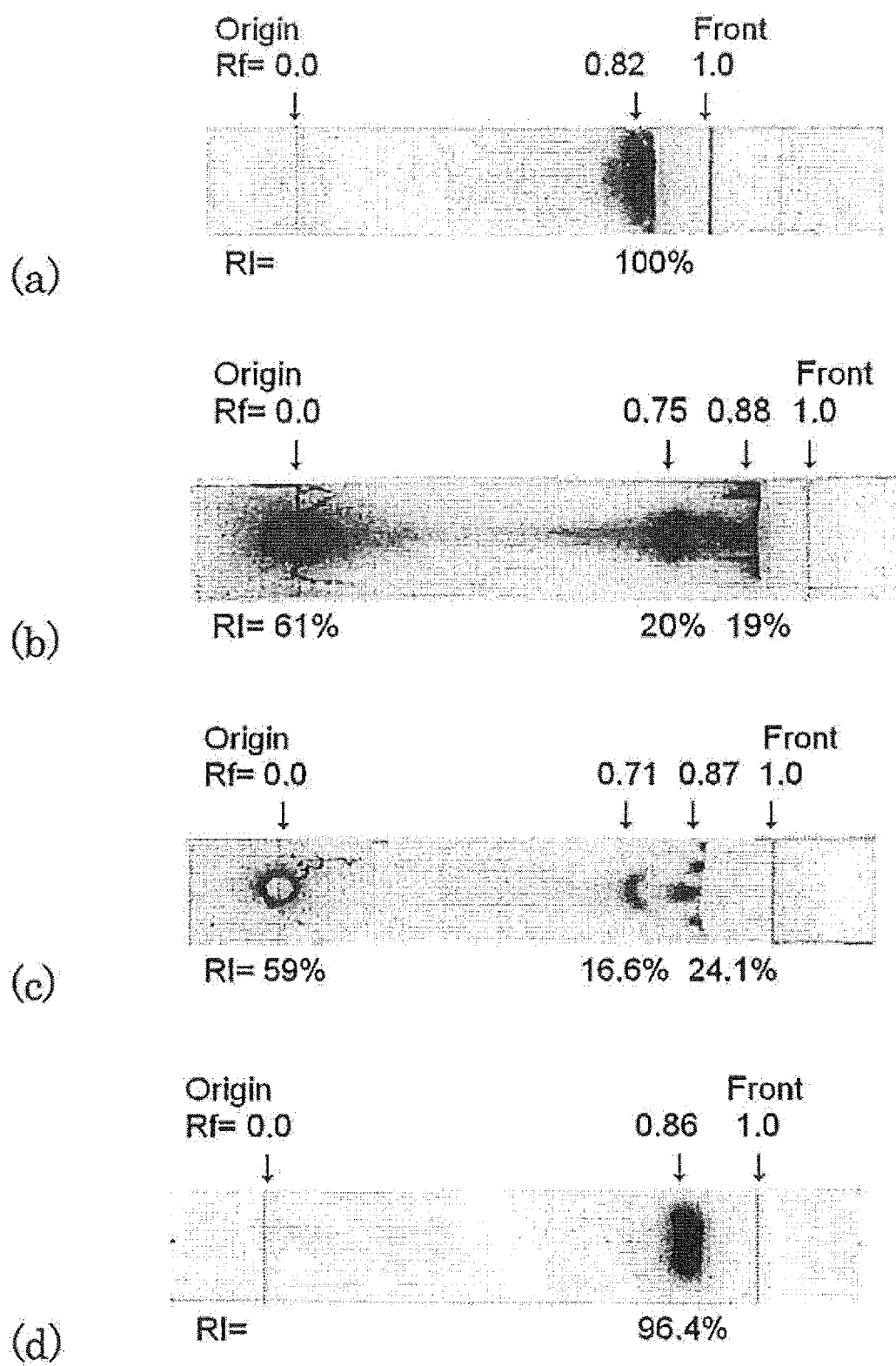
FIG. 1 shows the results of Experimental Example 1.

The present invention is explained in detail in the following.

The present invention relates to a production method of a solution containing $^{211}At^-$ (astatide ion) at a high radiochemical purity.

The method of the present invention is characterized by a step of adding a reducing agent to a solution (e.g., aqueous solution, alcohol solution (e.g., ethanol solution), alcohol aqueous solution (e.g., ethanol aqueous solution)) containing impurity derived from $^{211}At$ (hereinafter to be referred to as $^{211}At$ stock solution).

In the present specification, the impurity derived from $^{211}At$ refers to a compound derived from $^{211}A$ which is other than the target compound $^{211}At^-$ (astatide ion). Examples of the impurity derived from $^{211}At$ include oxides of astatine ($At^+$, $AtO^-$, $AtO_2^-$, $At(OH)$, $At(OH)_2^-$).

In the present invention, the content of the impurity derived from $^{211}At$ and contained in the $^{211}At$ stock solution is not particularly limited. A solution in which the radioactivity of the impurity derived from $^{211}At$ with respect to the radioactivity of the whole solution is more than 0% and up to 100% can be used as the $^{211}At$ stock solution of the present invention.

A $^{211}At$ solution (e.g., $^{211}At$ aqueous solution) obtained by a conventional method (e.g., the method described in the below-mentioned Reference Example 1) contains much impurity derived from $^{211}At$ and can be used as the $^{211}At$ stock solution in the method of the present invention.

The impurity derived from $^{211}At$ can be confirmed, for example, by thin layer chromatography described in the below-mentioned Experimental Example 1, or a method analogous thereto.

The reducing agent to be used in the method of the present invention is preferably a physiologically acceptable reducing agent. In the present invention, physiologically acceptable means being physiologically low toxic or nontoxic.

Examples of the reducing agent to be used in the method of the present invention include organic reducing agents (e.g., ascorbic acid, salt with ascorbic acid (e.g., salts of ascorbic acid with alkali metal or alkaline earth metal (e.g., sodium ascorbate, calcium ascorbate)), cysteine, glutathione, gentisic acid, glucose etc.), inorganic reducing agent (e.g., iron(II) sulfate), and ascorbic acid, salt with ascorbic acid (e.g., salts of ascorbic acid with alkali metal or alkaline earth metals (e.g., sodium ascorbate, calcium ascorbate)), cysteine, and glutathione are preferable, ascorbic acid, salts with ascorbic acid (e.g., salts of ascorbic acid with alkali metal or alkaline earth metals (e.g., sodium ascorbate, calcium ascorbate)) are more preferable, and ascorbic acid, sodium ascorbate are particularly preferable.

In the method of the present invention, the amount of the reducing agent to be used is an amount that achieves a final concentration of generally 0.1-30 wt % (w/v %), preferably 0.2-10 wt %, more preferably 0.5-5 wt %, with respect to a solution containing impurity derived from $^{211}At$ (that is, $^{211}At$ stock solution).

In the method of the present invention, the amount of the reducing agent to be used is generally 0.1-100 μmol, preferably 0.2-50 μmol, more preferably 1-12 μmol, with respect to 1 MBq of $^{211}At$ radioactivity of a solution containing impurity derived from $^{211}At$ (that is, $^{211}At$ stock solution).

In the method of the present invention, a solution e.g., aqueous solution, alcohol solution (e.g., ethanol solution), alcohol aqueous solution (e.g., ethanol aqueous solution)) containing the target $^{211}At^-$ (astatide ion) at a high radiochemical purity (e.g., not less than 30%) can be obtained by adding and mixing a reducing agent. The reducing agent may be dissolved in a solvent (e.g., water) in advance and added as a reducing agent solution (e.g., aqueous solution). The mixing can be performed by a known method. When the solution is mixed while aerating with an inert gas such as nitrogen, argon, etc. to block the contact with air and oxygen, the effect of the reducing agent is highly exhibited.

The reducing agent is added and mixed at room temperature, specifically 0-40° C., preferably 15-30° C. The mixing time is, for example, 5 min-2 hr, particularly, 10-30 min.

Production of the target $^{211}At^-$ (astatide ion) can be confirmed by thin layer chromatography.

The method of the present invention preferably further contains a step of adjusting to neutral or weakly alkaline by adding a pH adjuster or buffer. By adjusting to neutral or weakly alkaline, volatilization, transpiration of astatine, and generation of oxide can be prevented. The step can be performed by a known method. The pH adjuster may be dissolved in a solvent (e.g., water) in advance and added as a pH adjuster solution (e.g., an aqueous solution).

In the present specification, neutral or weakly alkaline generally means pH 5-pH 10, preferably pH 6-pH 9, more preferably pH 6.5-pH 8.5.

When the reducing agent used makes the solution neutral or weakly alkaline, it is not necessary to add a pH adjuster or a buffer.

In the method of the present invention, a pH adjusting agent or buffer generally used in pharmaceutical preparations can be used as the pH adjuster or buffer. For example, pH adjusts such as sodium hydrogen carbonate, hydrochloric acid, sodium hydroxide and the like, buffers such as phosphate buffer, acetate buffer, citrate buffer, borate buffer and the like can be mentioned, and sodium hydrogen carbonate is preferable.

In the present invention, an amount capable of adjusting to neutral or weakly alkaline can be appropriately selected as the amount of the pH adjuster or buffer.

In the method of the present invention, the order of the step of adding a reducing agent, and the step of adjusting to neutral or weakly alkaline by adding a pH adjuster or buffer is not particularly limited. A reducing agent and a pH regulator or buffer may be added simultaneously. From the aspect of preventing the risk of volatilization of astatine, it is preferable to perform the step of adding a reducing agent after the step of adjusting to neutral or weakly alkaline by adding a pH adjuster or buffer.

The method of the present invention may include a step of adding additives (e.g., solvents such as water for injection, saline, alcohol and the like, isotonicity agent, surfactant, sweetener, flavor, colorant, stabilizer, excipient) generally used for pharmaceutical preparations, in addition to the above-mentioned reducing agent, pH adjuster, and buffer. These additives are used in amounts conventionally used for pharmaceutical preparations.

Using the method of the present invention, a solution (e.g., aqueous solution, alcohol solution (e.g., ethanol solution), alcohol aqueous solution (e.g., ethanol aqueous solution) containing $^{211}At^-$ (astatide ion) at a high radiochemical purity (e.g., not less than 30%) can be produced.

In the present specification, the radiochemical purity is the ratio (%) of the radioactivity of $^{211}At^-$ (astatide ion) to the total radioactivity of $^{211}At$ in the solution.

The radiochemical purity of the solution containing $^{211}At^-$ (astatide ion) obtained by the method of the present invention is generally not less than 30%, preferably not less than 50%, more preferably not less than 80%, further preferably not less than 90%, further more preferably not less than 95%, particularly preferably 100%.

The radiochemical purity in the present invention can be confirmed by, for example, thin layer chromatography described in the below-mentioned Experimental Example 1, Experimental Example 8, or a method analogous thereto.

The embodiment of the method of the present invention is, for example, the following.

(1) A reducing agent (e.g., ascorbic acid), a pH adjuster (e.g., sodium hydrogen carbonate), and, where necessary, water for injection are added to a $^{211}At$ solution ($^{211}At$ stock solution), and they are mixed to give solution containing $^{211}At^-$ (astatide ion) at a high radiochemical purity.

(2) A reducing agent (e.g., sodium ascorbate), and, where necessary, water for injection are added to a $^{211}At$ solution ($^{211}At$ stock solution), and they are mixed to give solution containing $^{211}At^-$ (astatide ion) at a high radiochemical purity.

The present invention also relates to a solution (e.g., aqueous solution, alcohol solution (e.g., ethanol solution), for example, alcohol aqueous solution (e.g., ethanol aqueous solution)) containing $^{211}At^-$ (astatide ion) at a high radiochemical purity (e.g., not less than 30%), which is obtained by the above-mentioned production method of the present invention (hereinafter sometimes to be indicated as the high purity $^{211}At^-$-containing solution of the present invention) The definition and preferred range of the radiochemical purity are the same as above.

The high purity $^{211}At^-$-containing solution of the present invention may contain reducing agent, pH adjuster, buffer and the like added in the production step, and can be administered to the subject without separation. In addition, the high purity $^{211}At^-$-containing solution of the present invention may further contain additives generally used for pharmaceutical preparations.

The high purity $^{211}At^-$-containing solution of the present invention can be used for the treatment and diagnosis (particularly RI internal radiotherapy) of, for example, thyroid gland diseases (e.g., thyroid cancer, hyperthyroidism (Graves' disease) etc.), and thyroid cancer metastatic lesion in human and mammals (e.g., mouse, rat, rabbit, cat, dog, bovine, horse, monkey). The high purity $^{211}At^-$-containing solution of the present invention can also be used for the treatment and diagnosis (particularly RI internal radiotherapy) of cancers (e.g., stomach cancer, breast cancer, lung cancer, prostate cancer, colon cancer, ovarian cancer etc.) which are other than thyroid cancer and in which NIS is markedly expressed.

In the RI internal radiotherapy using the high purity $^{211}At^-$-containing solution of the present invention, the affected part can be treated by radiation of α-ray released by $^{211}At$ accumulated in the affected part after administration to patients.

The high purity $^{211}At^-$-containing solution of the present invention can be safely administered orally or parenterally (intravenous injection, drip etc.).

The dose of the high purity $^{211}At^-$-containing solution of the present invention varies depending on the subject of administration, administration route, disease and the like. For example, when it is used for treatment of thyroid cancer in an adult, the dose of $^{211}At^-$ (astatide ion) is 1 MBq-20 GBq.

EXAMPLE

The present invention is explained in more detail in the following by referring to Examples and Experimental Examples, which are not to be construed as limitative.

In Examples, % showing the concentration of components in the solution is wt % (w/v %).

Reference Example 1: Preparation of $^{211}At$ Aqueous Solution

Helium (28 MeV, 1-2 ρA) accelerated by a cyclotron was irradiated to the target substance bismuth-209 ($^{209}Bi$), and astatine-211 ($^{211}At$) was produced in the target substance by a nuclear reaction of $^{209}Bi(\alpha,2n)^{211}At$. After irradiation, the target substance was dissolved by heating in an electric heating appliance to 800° C., and $^{211}At$ evaporating from the target substance was dissolved in a small amount of water (0.1-2 mL) to prepare a $^{211}At$ aqueous solution. The radioactivity of this $^{211}At$ aqueous solution on preparation was 5-25 MBq.

Reference Example 2: Preparation of Sodium Hydrogen Carbonate-Added $^{211}At$ Aqueous Solution To the $^{211}At$ aqueous solution (0.1 mL, 14 MBq) prepared in Reference Example 1 were successively added water for injection (0.5 mL) and 7% sodium hydrogen carbonate aqueous solution (0.8 mL), and the mixture was stirred at room temperature for 30 min to prepare a sodium hydrogen carbonate-added $^{211}$At aqueous solution (pH 7.5-9.0).

Example 1: Preparation of 0.9% Ascorbic Acid-Added $^{211}$At Aqueous Solution

To the $^{211}$At aqueous solution (0.1 mL, 25 MBq) prepared in Reference Example 1 were successively added water for injection (0.5 mL), 7% sodium hydrogen carbonate aqueous solution (0.8 mL), and 2% ascorbic acid aqueous solution (1.2 mL), and the mixture was stirred at room temperature for 30 min to prepare a 0.9% ascorbic acid-added $^{211}$At aqueous solution (pH 7.5-9.0).

Experimental Example 1: Analysis of Radiochemical Purity

The radiochemical purity of the 0.9% ascorbic acid-added $^{211}$At aqueous solution prepared in Example 1, $^{211}$At aqueous solution prepared in Reference Example 1, sodium hydrogen carbonate-added $^{211}$At aqueous solution prepared in Reference Example 2, and Na$^{123}$I aqueous solution (manufactured by FUJIFILM RI Pharma Co., Ltd.) as a comparison control was analyzed by thin layer chromatography (TLC) according to the following method.

Each sample (2 µL) was applied to the original line (Origin) of a thin-layer plate (G60, manufactured by Merck & Co., Inc.) and developed with a mixed solution of acetonitrile:water:trifluoroacetic acid (67:33:0.5) as a developing solvent. After exposure to an imaging plate (BAS IP, GE Healthcare), the distribution ratio (%) of the radioactivity on the thin-layer plate was measured by a bioimaging device (TYPHOON7000, manufactured by GE Healthcare). The results are shown in FIG. 1.

In the 0.9% ascorbic acid-added $^{211}$At aqueous solution of Example 1 (FIG. 1, (a)), a radioactive spot corresponding to $^{211}$At-astatide ion ($^{211}$At$^-$) was detected at the position of Rf=0.82 with 100% radiochemical purity. The fact that this radioactive spot is $^{211}$At$^-$ was considered appropriate by inferring from the radioactive spot of $^{123}$I-iodide ion ($^{123}$I$^-$) in the Na$^{123}$I aqueous solution (Rf value of (d)=0.86 in FIG. 1) obtained under the same conditions. In contrast, in the $^{211}$At aqueous solution of Reference Example 1 (FIG. 1, (b)) and sodium hydrogen carbonate-added $^{211}$At aqueous solution of Reference Example 2 (FIG. 1, (c)), the radiochemical purity of $^{211}$At$^-$ was not more than 20% in both, and most of the radioactivity was detected as a plurality of radioactive impurities near the point of origin and near the solvent tip (Front). From the above results, it was shown that highly pure $^{211}$At$^-$ is produced when ascorbic acid is added to the $^{211}$At aqueous solution.

Examples 2-5: Preparation of 0.25-2% Ascorbic Acid-Added $^{211}$At Aqueous Solution To the $^{211}$At aqueous solution (0.1 mL) prepared in Reference Example 1 were added an appropriate amount of water for injection, 7% sodium hydrogen carbonate aqueous solution, and 4% ascorbic acid aqueous solution, and the mixture was stirred at room temperature for 30 min to respectively prepare ascorbic acid-added $^{211}$At aqueous solutions (pH 7.5-9.0) having a final concentration of 0.25% (Example 2), 0.5% (Example 3), 1% (Example 4) or 2% (Example 5). The final radioactivity concentrations of $^{211}$At were all standardized to 10 MBq/mL.

Experimental Example 2: Study of Effect of Ascorbic Acid Concentration (0.25-2%)

Figure 2:
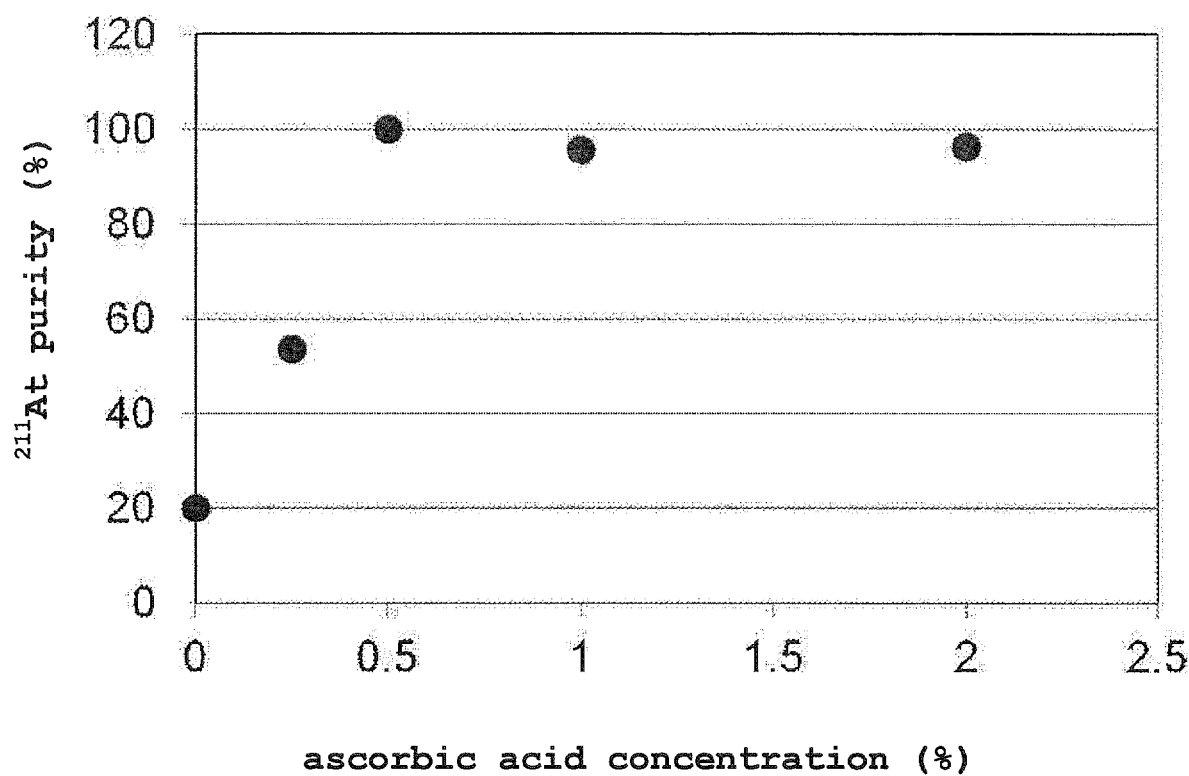
FIG. 2 shows the results of Experimental Example 2.

The radiochemical purity of the ascorbic acid-added $^{211}$At aqueous solutions of Examples 2-5 was analyzed by TLC according to a method similar to that in Experimental Example 1. The results are shown in FIG. 2.

When ascorbic acid was not added ($^{211}$At aqueous solution of Experimental Example 1), the radiochemical purity of $^{211}$At$^-$ was 20%, whereas the radiochemical purity of $^{211}$At$^-$ increased to 53.8% when the ascorbic acid concentration was 0.25%, and further, the radiochemical purity of $^{211}$At$^-$ was not less than 95% when the ascorbic acid concentration was not less than 0.5%.

Example 6: Preparation of 1% Sodium Ascorbate-Added $^{211}$At Aqueous Solution

To the $^{211}$At aqueous solution (0.1 mL, 2 MBq) prepared in Reference Example 1 was added 2% sodium ascorbate aqueous solution (0.1 mL), and the mixture was stirred at room temperature for 30 min to prepare a 1% ascorbate-added $^{211}$At aqueous solution (pH 5-7).

Experimental Example 3: Analysis of Radiochemical Purity

Figure 3:
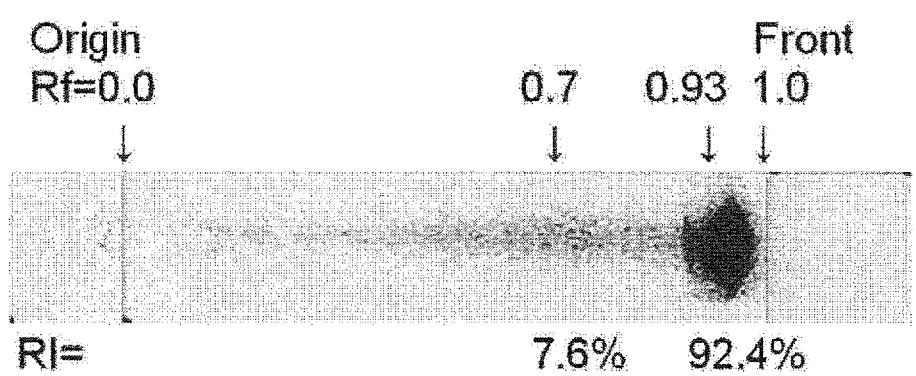
FIG. 3 shows the results of Experimental Example 3.

The radiochemical purity of the 1% sodium ascorbate-added $^{211}$At aqueous solution of Example 6 was analyzed by TLC according to a method similar to that in Experimental Example 1. The results are shown in FIG. 3.

The radiochemical purity of $^{211}$At$^-$ (Rf=0.93) was 92.4%. It was found that sodium ascorbate is effective for producing $^{211}$At$^-$ having high purity similar to that of ascorbic acid.

Example 7: Preparation of 1% Cysteine-Added $^{211}$At Aqueous Solution

To the $^{211}$At aqueous solution (0.1 mL, 4 MBq) prepared in Reference Example 1 were added water for injection (0.05 mL), 7% sodium hydrogen carbonate aqueous solution (0.1 mL), and 2% cysteine aqueous solution (0.25 mL), and the mixture was stirred at room temperature for 30 min to prepare a 1% cysteine-added $^{211}$At aqueous solution (pH 7-9).

Experimental Example 4: Analysis of Radiochemical Purity

Figure 4:
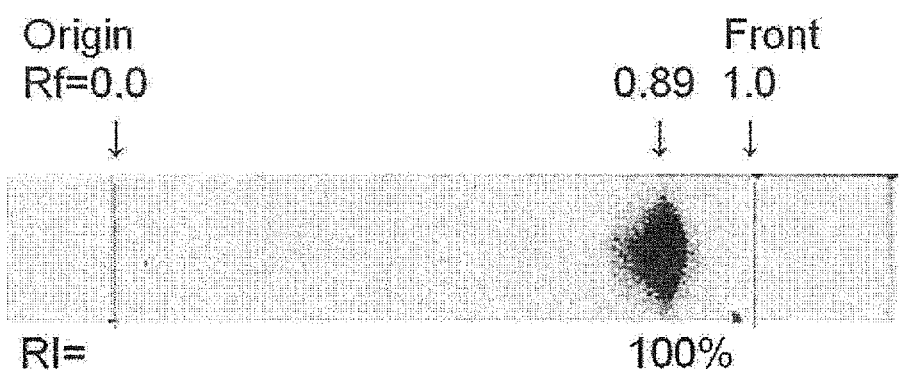
FIG. 4 shows the results of Experimental Example 4.

The radiochemical purity of the 1% cysteine-added $^{211}$At aqueous solution of Example 7 was analyzed by TLC according to a method similar to that in Experimental Example 1. The results are shown in FIG. 4.

The radiochemical purity of $^{211}$At$^-$ (Rf=0.89) was 100%. It was found that cysteine is effective for producing $^{211}$At$^-$ having high purity similar to that of ascorbic acid.

Example 8: Preparation of 1% Glutathione Addition $^{211}$At Aqueous Solution

To the $^{211}$At aqueous solution (0.1 mL, 4 MBq) prepared in Reference Example 1 were added water for injection (0.05 mL), 7% sodium hydrogen carbonate aqueous solution (0.1 mL), and 2% glutathione aqueous solution (0.25 mL), and the mixture was stirred at room temperature for 30 min to prepare a 1% glutathione-added $^{211}$At aqueous solution (pH 7-9).

Experimental Example 5: Analysis of Radiochemical Purity

Figure 5:
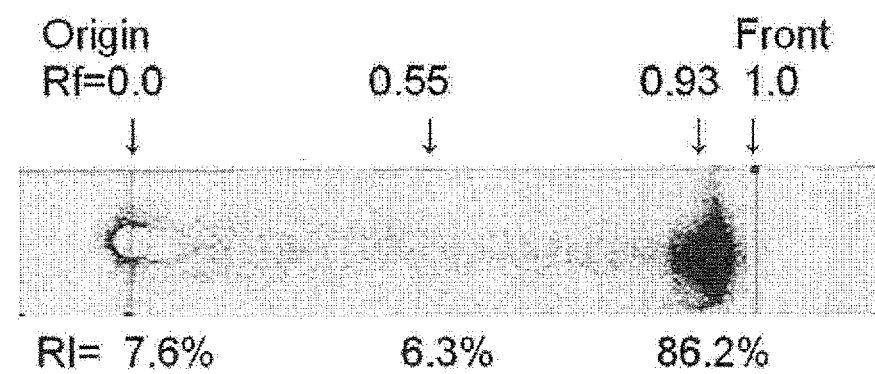
FIG. 5 shows the results of Experimental Example 5.

The radiochemical purity of the 1% glutathione-added $^{211}$At aqueous solution of Example 8 was analyzed by TLC according to a method similar to that in Experimental Example 1. The results are shown in FIG. 5.

The radiochemical purity of $^{211}$At⁻ (Rf=0.93) was 86.2%. It was found that glutathione is effective for producing $^{211}$At⁻ having high purity similar to that of ascorbic acid.

Experimental Example 6: Planar Imaging of Normal Rat

Figure 6:
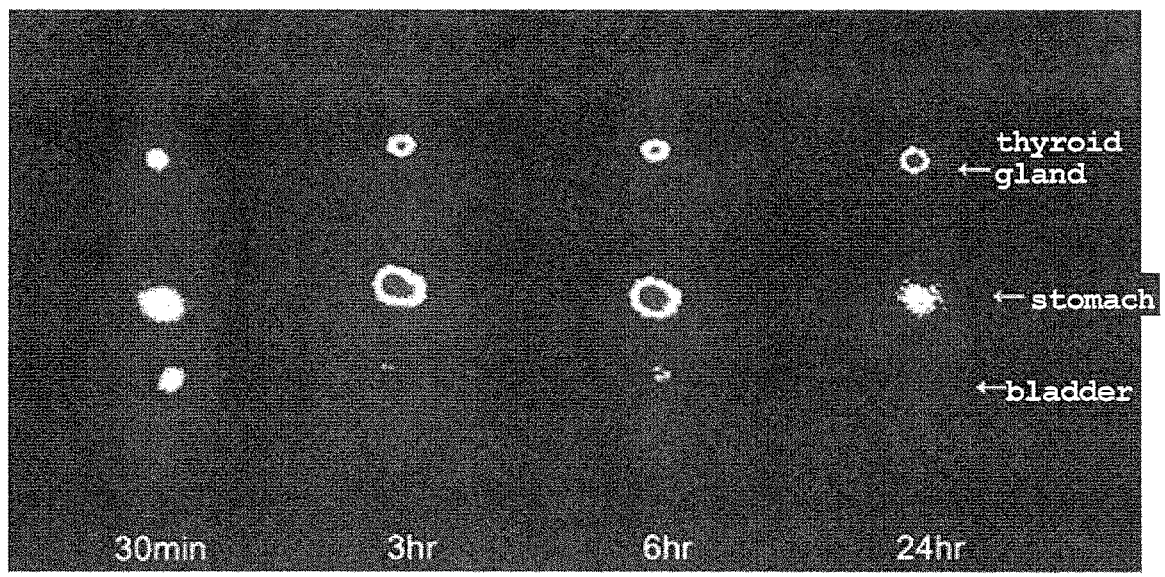
FIG. 6 shows the results of Experimental Example 6.
Figure 6:
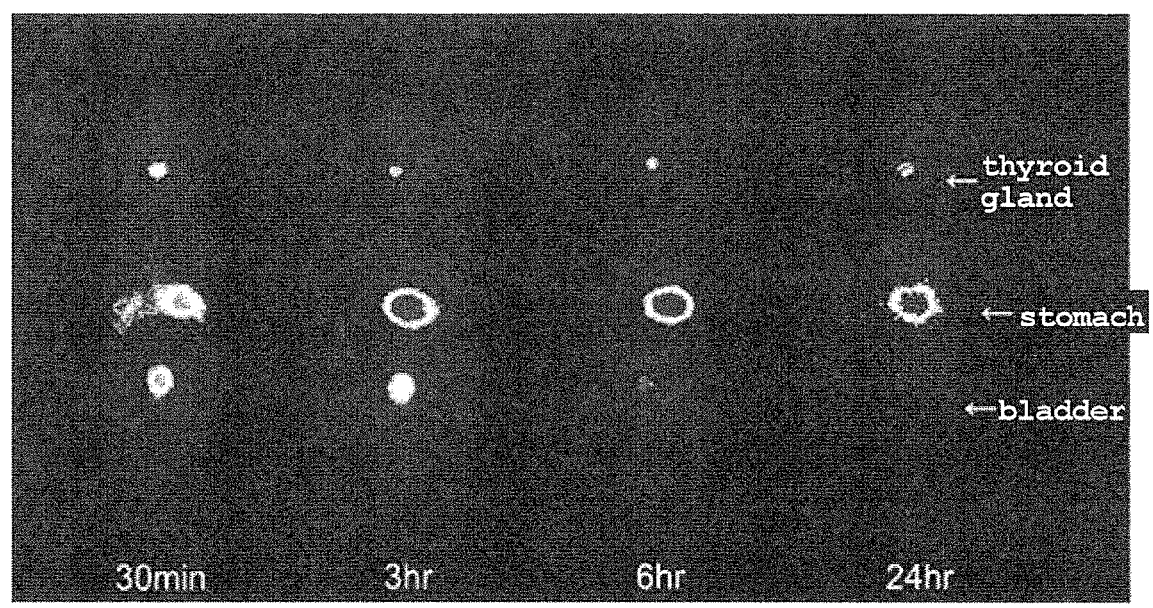

Normal rats (Wistar rat, male, 3 months old) fed with a low iodine diet for 2 weeks were used for the experiment. The rat was anesthetized with isoflurane, and the 0.9% ascorbic acid-added $^{211}$At aqueous solution (about 3 MBq/rat) prepared in Example 1 was administered into the tail vein (n=3). As a control group, similarly-treated rats were administered with the $^{211}$At aqueous solution (about 5 MBq/rat) prepared in Reference Example 1 (n=3). The rats were anesthetized 30 min, 3 hr, 6 hr, and 24 hr after administration, and planar images were taken with a gamma camera (E.CAM, manufactured by Siemens) Imaging time was 10 min in the case of 30 min to 6 hr after administration, and 20 min in the case of 24 hr after administration. FIG. 6 shows the results of planar imaging.

In FIG. 6, the ascorbic acid group (0.9% ascorbic acid-added $^{211}$At aqueous solution administration group) in the upper panel (a) showed strong accumulation of radioactivity in the thyroid gland from the early stage (30 min point) after administration of the test solution as compared to the control group ($^{211}$At aqueous solution administration group) in the lower panel (b), and the accumulation of radioactivity was enhanced with time until the 24 hr point. Other than the thyroid gland, accumulation in the stomach and excretion into the urinary system (bladder) were shown. In the control group of (b), the accumulation of radioactivity in the thyroid gland was slightly weak, and retention of radioactivity in the stomach was shown. From the above results, it was suggested that administration of a $^{211}$At⁻ aqueous solution prepared to have a high purity by the addition of ascorbic acid to rats enhances the accumulation of radioactivity in the thyroid gland and, on the other hand, reduces the non-specific accumulation in the stomach.

Experimental Example 7: Normal Rat Body Distribution Test

After completion of the imaging at 24 hr point after administration described in Experimental Example 6, the rats in the ascorbic acid group (0.9% ascorbic acid-added $^{211}$At aqueous solution administration group) and the control group ($^{211}$At aqueous solution administration group) were dissected, and the thyroid gland, stomach, and other major organs were removed. The wet weight of each excised organ was measured with a microbalance, and the radioactivity was measured with a gamma counter (2480WIZARD², manufactured by Perkin Elmer Co., Ltd.). Table 1 shows the results of the body distribution test in normal rats (radioactivity count per organ weight). In both groups, the radioactivity count of the thyroid gland was 10 times or higher than that of other organs. In the ascorbic acid group, the radioactivity count of the thyroid gland was about 4 times higher than that of the control group. On the other hand, the radioactive count of the stomach, spleen and liver was higher in the control group than the ascorbic acid group.

Table 2 shows the results of calculation of the radioactivity count ratio per unit weight of the thyroid gland and other organs from the values in Table 1. In both the ascorbic acid group and the control group, the radioactivity count ratio of the thyroid gland and other major organs was as high as 19.3-fold to 2755.6-fold. The thyroid gland/stomach ratio was 4.9 times higher in the ascorbic acid group than in the control group. From the above results, it was suggested that administration of a $^{211}$At⁻ aqueous solution prepared to have a high purity by the addition of ascorbic acid to rats enhances the accumulation of radioactivity in the thyroid gland and reduces the non-specific accumulation in the stomach and other organs. That is, it was suggested that an ascorbic acid-added $^{211}$At aqueous solution enhances the therapeutic effect on thyroid cancer, reduces exposure of other organs such as the stomach to radiation, and enables safer treatment.

TABLE 1

Normal rat body distribution test results (at 24 hr point from administration): radioactivity count (unit: counts/g) per weight of each organ

| organ | test solution group | |
|---|---|---|
| | ascorbic acid group (n = 3) | control group (n = 3) |
| thyroid gland | 13097067 | 3283443 |
| stomach | 139652 | 169690 |
| spleen | 43518 | 57081 |
| liver | 4753 | 11729 |

TABLE 2

Rat body distribution test results (at 24 hr point from administration): radioactivity count ratio per unit weight of thyroid gland and other organs (stomach, spleen, and liver)

| organ | test solution group | | |
|---|---|---|---|
| | ascorbic acid group (n = 3) | control group (n = 3) | ascorbic acid group/control group |
| thyroid gland/stomach | 93.8 | 19.3 | 4.9 |
| thyroid gland/spleen | 300.9 | 57.5 | 5.2 |
| thyroid gland/liver | 2755.6 | 280.0 | 9.9 |

Examples 9-12: Preparation of Reducing Agent-Added $^{211}$At Aqueous Solution

The $^{211}$At aqueous solution prepared in Reference Example 1 was diluted with water and to the prepared crudely purified $^{211}$At aqueous solution 0.1 mL (about 1 MBq) was added 2% reducing agent (ascorbic acid, cysteine, glutathione or iron(II) sulfate) aqueous solution (0.1 mL), and the mixture was stirred at room temperature for 1 hr to prepare ascorbic acid-added $^{211}$At aqueous solution (Example 9), cysteine-added $^{211}$At aqueous solution (Example 10), glutathione-added $^{211}$At aqueous solution (Example 11), and iron(II) sulfate-added $^{211}$At aqueous solution (Example 12), each having a final concentration of the reducing agent of 1%.

Figure 7:
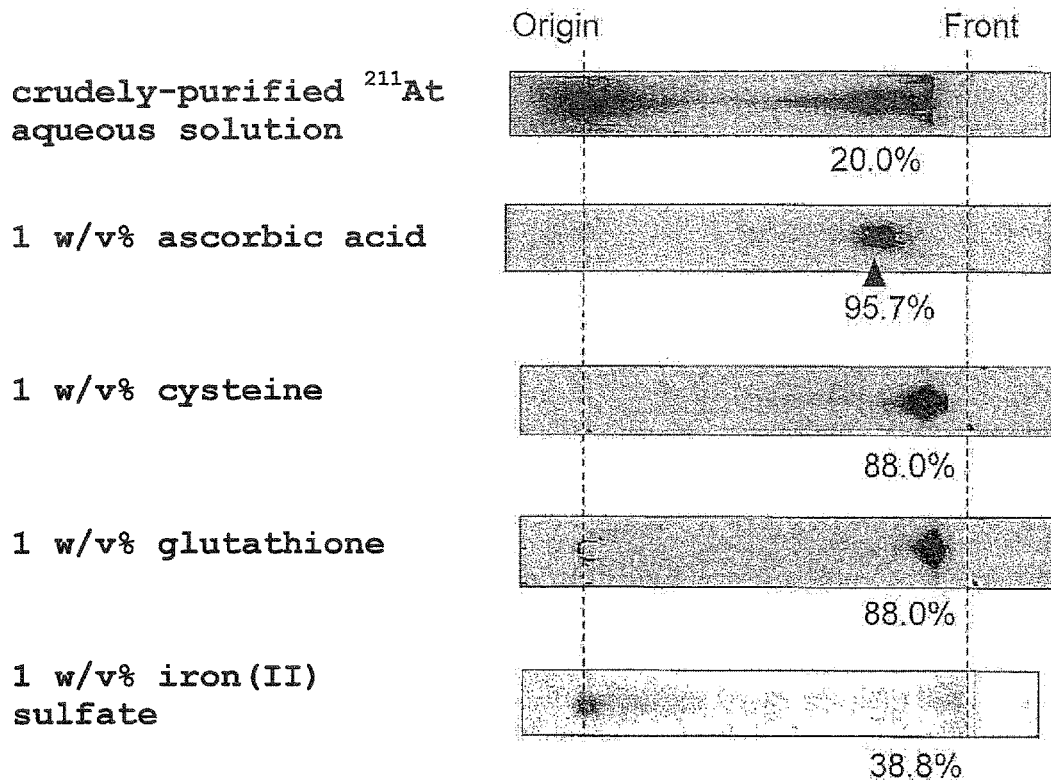
FIG. 7 shows the results of Experimental Example 8.

Experimental Example 8: Analysis of Radiochemical Purity: Effect of Addition of Various Reducing Agents A crudely-purified $^{211}$At aqueous solution, and the reducing agent-added $^{211}$At aqueous solutions prepared in Examples 9-12 were analyzed by TLC (thin-layer plate: silica gel G60F$_{254}$ (manufactured by Merck), solvent: acetonitrile-water-trifluoroacetic acid (67/33/0.1)) (FIG. 7). The radiochemical purity of $^{211}$At$^-$ (astatide ion) was the highest (95.7%) when ascorbic acid was used, and then in the order of cysteine, glutathione, and iron(II) sulfate.

Experimental Example 9: Comparison of Intracellular Uptake of $^{211}$At by K1 Cell (Human Thyroid Cancer Cell) and K1-NIS Cell (NIS Expression K1 Cell)

Figure 8:
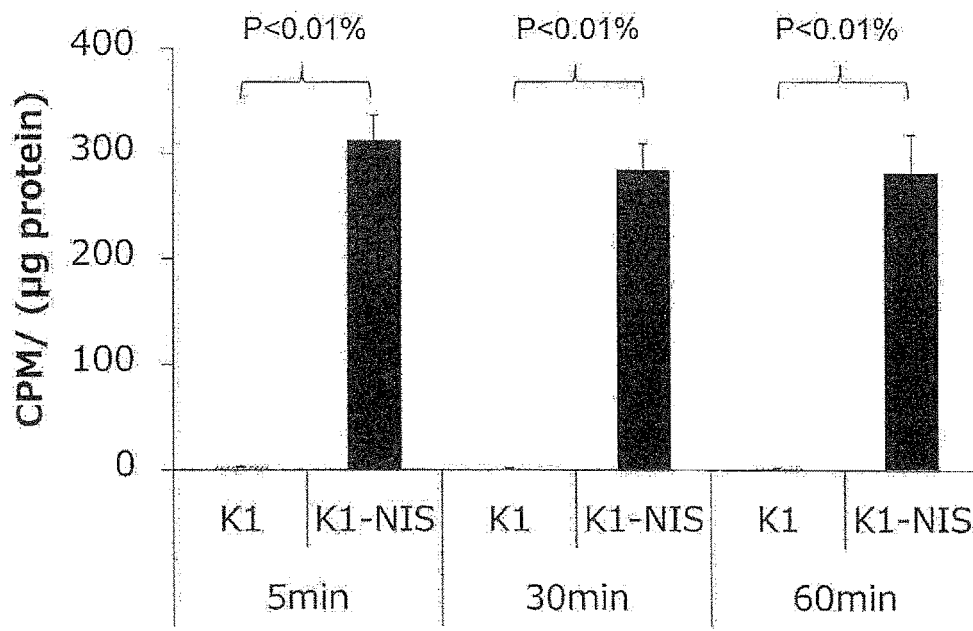
FIG. 8 shows the results of Experimental Example 9.

K1 cells (human thyroid cancer cell) and K1-NIS cells (NIS expression K1 cells), each 1×10$^5$ cells, were seeded on a 96-well plate, and 10 μL (about 10 kBq) of $^{211}$At aqueous solution was added. The cells were cultured at 37° C. for 5, 30, and 60 min, lysed with 0.1N NaOH, and the intracellular radioactivity was measured with a gamma counter (2480 Wizard2, Perkin Elmer). The amount of protein was measured with a BCA protein quantification kit (FUJIFILM Corporation) and a plate reader (Thermo Fisher). As shown in FIG. 8, $^{211}$At was taken up by KI-NIS cells but was not taken up by KI cells. It was shown that $^{211}$At is specifically taken up intracellularly via NIS.

Experimental Example 10: Changes in Time-Course Uptake Amount of $^{211}$At-AA(+) and $^{211}$At-AA(−) by Thyroid Cancer Cell (K1-NIS)

The $^{211}$At aqueous solution prepared in Reference Example 1 was diluted with water to prepare astatine aqueous solution ($^{211}$At-AA(−), 1 MBq/mL) without ascorbic acid. In addition, the $^{211}$At aqueous solution prepared in Reference Example 1 was diluted with water, and ascorbic acid was further added to a final concentration of 1% to prepare ascorbic acid-added astatine aqueous solution ($^{211}$At-AA(+), 1 MBq/mL).

Figure 9:
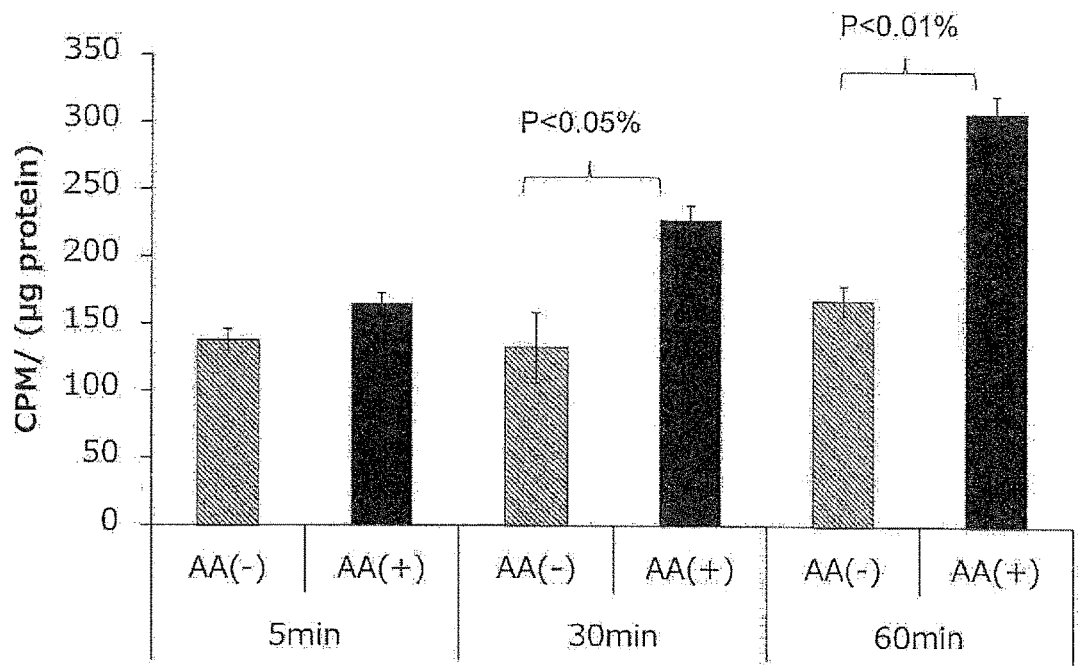
FIG. 9 shows the results of Experimental Example 10.

K1-NIS cells (NIS expressing K1 cells) were seeded on a 96-well plate by 1×10$^5$ cells, and 10 μL (about 10 kBq) of ascorbic acid-added astatine aqueous solution ($^{211}$At-AA(+)) or astatine aqueous solution ($^{211}$At-AA(−)) without ascorbic acid was added. The cells were cultured at 37° C. for 5, 30, or 60 min, lysed with 0.1N NaOH, and the intracellular radioactivity was measured with a gamma counter (2480 Wizard2, Perkin Elmer). The amount of protein was measured with a BCA protein quantification kit (FUJIFILM Corporation) and a plate reader (Thermo Fisher). As shown in FIG. 9, the uptake amount of $^{211}$At-AA(+) by K1-NIS cells increased over time and reached about 2 times that of AA(−) (60 min later). It was shown that addition of ascorbic acid to the $^{211}$At aqueous solution increases $^{211}$At uptake amount of the cell.

Experimental Example 11: SPECT Imaging of Mice Transplanted with Thyroid Cancer Cell (K1-NIS) by $^{211}$At-AA(+)

The $^{211}$At aqueous solution prepared in Reference Example 1 was diluted with water, and ascorbic acid was further added to a final concentration of 1% to prepare $^{211}$At-AA(+) aqueous solution.

Figure 10:
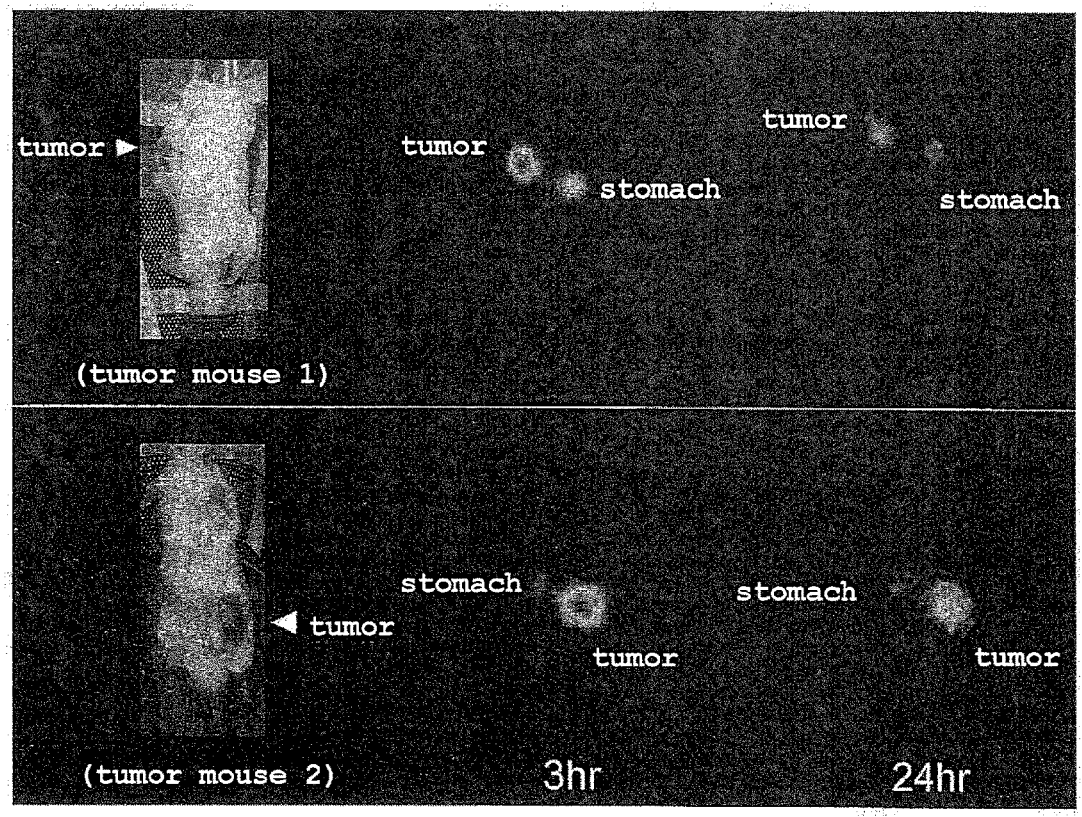
FIG. 10 shows the results of Experimental Example 11.

A thyroid cancer-transplanted mouse was prepared by injecting 1×10$^7$ K1-NIS cells subcutaneously into SCID mouse. A $^{211}$At-AA(+) aqueous solution (1 MBq) was intravenously injected to this mouse, and images were taken with a SPECT camera (E-cam, Siemens) after 3 hr and 24 hr. The tumor site was clearly depicted at any time point (FIG. 10). The radioactivity accumulation rate at the tumor site was 22.5±10.4% (3 hr later) and 12.9±6.8% (24 hr later). In addition, weak physiological accumulation of radioactivity was also observed in the stomach. This result suggests that $^{211}$At-AA(+) is useful for diagnosis and treatment of NIS-expressing tumors including thyroid cancer.

Experimental Example 12: Treatment of Thyroid Cancer Cell (K1-NIS)-Transplanted Mouse by $^{211}$At-AA(+) Aqueous Solution: Changes in Tumor Size and Body Weight Over Time after Single Intravenous Injection of 0.1 MBq, 0.4 MBq and 1 MBq The $^{211}$At$^-$ aqueous solution prepared in Reference Example 1 was diluted with water, and ascorbic acid was further added to a final concentration of 1% to prepare $^{211}$At-AA(+) aqueous solution.

Figure 11:
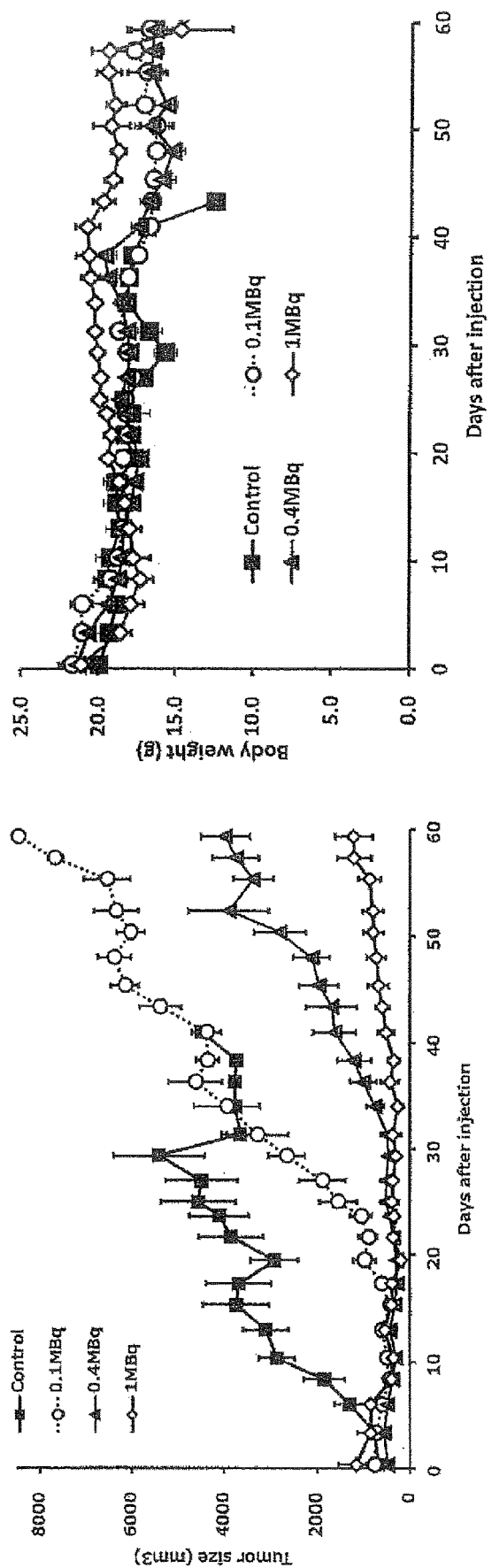
FIG. 11 shows the results of Experimental Example 12.

A thyroid cancer-transplanted mouse was prepared by injecting 1×10$^7$ K1-NIS cells subcutaneously into SCID mouse. A $^{211}$At-AA(+) aqueous solution (1 MBq, 0.4 MBq, and 1 MBq) was intravenously injected once to this mouse, and changes in the tumor size and body weight were measured for 60 days (n=6). As shown in FIG. 11a (FIG. 11, left figure), the tumor size increased over time in the non-treated group (control), but tumor reduction or growth suppressive effect was observed for about 40 days in the $^{211}$At 1 MBq intravenous injection group. The tumor growth suppressive effect was dependent on the amount of radioactivity of $^{211}$At. As shown in FIG. 11b (FIG. 11, right figure.), transient weight loss was initially observed, but it was recovered later in the 1 MBq intravenous injection group. The body weight of the 0.1 MBq group and the 0.4 MBq group did not differ much as compared to that of the control group.

INDUSTRIAL APPLICABILITY

The present invention can provide a solution containing $^{211}$At$^-$ (astatide ion) at a high radiochemical purity, that is useful for RI internal radiotherapy and the like for the treatment of thyroid gland disease and the like.

This application is based on patent application No. 2017-255109 filed in Japan, the contents of which are encompassed in full herein.

The invention claimed is:

1. A method for producing an aqueous solution, an ethanol solution, or an aqueous ethanol solution, comprising $^{211}$At$^-$ at a radiochemical purity of not less than 90% by using $^{211}$At obtained by a nuclear reaction as a starting material, the method comprising a step of adding a reducing agent selected from the group consisting of ascorbic acid and a salt of ascorbic acid to an aqueous solution, an ethanol solution, or an aqueous ethanol solution comprising an impurity derived from $^{211}$At, wherein the reducing agent is added at a final concentration of 0.5 wt % or higher with respect to the aqueous solution, ethanol solution, or aqueous ethanol solution comprising an impurity derived from $^{211}$At.

2. The method according to claim 1, wherein the reducing agent is ascorbic acid or sodium ascorbate.

3. The method according to claim 2, further comprising a step of adjusting to neutral or weakly alkaline by adding a pH adjuster or buffer.

4. The method according to claim 1, further comprising a step of adjusting to neutral or weakly alkaline by adding a pH adjuster or buffer.

5. An aqueous solution, an ethanol solution, or an aqueous ethanol solution comprising $^{211}At^-$ at a radiochemical purity of not less than 90% and a reducing agent selected from the group consisting of ascorbic acid and a salt of ascorbic acid, wherein the solution is produced by the method according to claim 1.

6. An aqueous solution, an ethanol solution, or an aqueous ethanol solution comprising $^{211}At^-$ at a radiochemical purity of not less than 90% and a reducing agent selected from the group consisting of ascorbic acid and a salt of ascorbic acid, wherein the solution is produced by the method according to claim 2.

7. An aqueous solution, an ethanol solution, or an aqueous ethanol solution comprising $^{211}At^-$ at a radiochemical purity of not less than 90% and a reducing agent selected from the group consisting of ascorbic acid and a salt of ascorbic acid, wherein the solution is produced by the method according to claim 3.

8. An aqueous solution, an ethanol solution, or an aqueous ethanol solution comprising $^{211}At^-$ at a radiochemical purity of not less than 90% and a reducing agent selected from the group consisting of ascorbic acid and a salt of ascorbic acid, wherein the solution is produced by the method according to claim 4.

9. The method according to claim 1, further comprising a step of adjusting to neutral or weakly alkaline by adding sodium hydrogen carbonate.

10. The method according to claim 2, further comprising a step of adjusting to neutral or weakly alkaline by adding sodium hydrogen carbonate.

11. An aqueous solution, an ethanol solution, or an aqueous ethanol solution comprising $^{211}At^-$ at a radiochemical purity of not less than 90%, and a reducing agent selected from the group consisting of ascorbic acid and a salt of ascorbic acid, wherein the solution is produced by the method according to claim 9.

12. An aqueous solution, an ethanol solution, or an aqueous ethanol solution comprising $^{211}At^-$ at a radiochemical purity of not less than 90% and a reducing agent selected from the group consisting of ascorbic acid and a salt of ascorbic acid, wherein the solution is produced by the method according to claim 10.

* * * * *